US009809505B1

(12) United States Patent
Buchanan et al.

(10) Patent No.: US 9,809,505 B1
(45) Date of Patent: Nov. 7, 2017

(54) PRODUCTION OF AROMATICS FROM METHANOL AND CO-FEEDS

(71) Applicant: ExxonMobil Chemical Patents Inc., Baytown, TX (US)

(72) Inventors: John S. Buchanan, Flemington, NJ (US); Stephen H. Brown, Lebanon, NJ (US); Lorenzo C. DeCaul, Langhorne, PA (US); Brett T. Loveless, Houston, TX (US); Rohit Vijay, Bridgewater, NJ (US); Stephen J. McCarthy, Center Valley, PA (US); Michel Daage, Hellertown, PA (US); Mayank Shekhar, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/646,889

(22) Filed: Jul. 11, 2017

Related U.S. Application Data (62) Division of application No. 14/829,399, filed on Aug. 18, 2015, now Pat. No. 9,732,013.

(60) Provisional application No. 62/057,855, filed on Sep. 30, 2014.

(51) Int. Cl.
*C07C 1/20* (2006.01)
*C07C 1/207* (2006.01)
*C10G 3/00* (2006.01)

(52) U.S. Cl.
CPC .............. *C07C 1/20* (2013.01); *C07C 1/2076* (2013.01); *C10G 3/49* (2013.01); *C07C 2529/44* (2013.01); *C10G 2400/30* (2013.01)

(58) Field of Classification Search
CPC ....................................... C07C 1/20

USPC ................ 585/469, 638, 639, 640, 240
See application file for complete search history.

(56) References Cited

U.S. PATENT DOCUMENTS

| | | |
|---|---|---|
| 3,894,102 A | 7/1975 | Chang et al. |
| 3,894,103 A | 7/1975 | Chang et al. |
| 3,894,104 A | 7/1975 | Chang et al. |
| 3,894,107 A | 7/1975 | Butter et al. |
| 3,928,483 A | 12/1975 | Chang et al. |
| 3,960,978 A | 6/1976 | Givens et al. |
| 3,998,898 A | 12/1976 | Chang et al. |
| 4,021,502 A | 5/1977 | Plank et al. |
| 4,025,571 A | 5/1977 | Lago |
| 4,035,430 A | 7/1977 | Dwyer et al. |
| 4,049,573 A | 9/1977 | Kaeding |
| 4,058,576 A | 11/1977 | Chang et al. |

(Continued)

FOREIGN PATENT DOCUMENTS

| | | |
|---|---|---|
| GB | 1526461 A | 9/1978 |
| WO | 2007/020068 A1 | 2/2007 |

*Primary Examiner* — Thuan D Dang (57) ABSTRACT

Methods are provided for improving the yield of aromatics during conversion of oxygenate feeds. An oxygenate feed can contain a mixture of oxygenate compounds, including one or more compounds with a hydrogen index of less than 2, so that an effective hydrogen index of the mixture of oxygenates is between about 1.4 and 1.9. Methods are also provided for converting a mixture of oxygenates with an effective hydrogen index greater than about 1 with a pyrolysis oil co-feed. The difficulties in co-processing a pyrolysis oil can be reduced or minimized by staging the introduction of pyrolysis oil into a reaction system. This can allow varying mixtures of pyrolysis oil and methanol, or another oxygenate feed, to be introduced into a reaction system at various feed entry points.

13 Claims, 3 Drawing Sheets

(56) References Cited

U.S. PATENT DOCUMENTS

| | | |
|---|---|---|
| 4,085,155 A | 4/1978 | Goodwin |
| 4,088,706 A | 5/1978 | Kaeding |
| 4,150,062 A | 4/1979 | Garwood et al. |
| 4,211,640 A | 7/1980 | Garwood et al. |
| 4,227,992 A | 10/1980 | Garwood et al. |
| 4,260,841 A | 4/1981 | Holland et al. |
| 4,423,274 A | 12/1983 | Daviduk et al. |
| 4,433,185 A | 2/1984 | Tabak |
| 4,433,189 A | 2/1984 | Young |
| 4,445,031 A | 4/1984 | Kamoshida |
| 4,456,779 A | 6/1984 | Owen et al. |
| 7,820,867 B2 | 10/2010 | Joensen et al. |
| 2014/0128639 A1 | 5/2014 | Powell et al. |

|  | Comparative Bio-Oil Mass% |
|---|---|
| Water | 21.0 |
| Acetone | 4.0 |
| Alcohols | |
| Methanol | 2.6 |
| Ethanol | 1.4 |
| Isopropanol | 0.0 |
| Syringols | 5.0 |
| Furans | 6.0 |
| Phenols | 7.0 |
| Sugars | 8.0 |
| Guaiacols | 8.0 |
| Aldehydes | |
| Formaldehyde | 4.0 |
| Acetaldeyhde | 6.0 |
| Acids | |
| Formic | 5.6 |
| Acetic | 8.4 |
| Hydroxyacetaldehyde | 9.1 |
| Acetol | 3.9 |

FIG. 3

PRODUCTION OF AROMATICS FROM METHANOL AND CO-FEEDS

PRIORITY CLAIM

This application is a divisional of U.S. patent application Ser. No. 14/829,399, filed Aug. 18, 2015, which further claims priority to and the benefit of U.S. Provisional Application No. 62/057,855, filed Sep. 30, 2014, the disclosure of each are incorporated herein by reference in their entireties.

FIELD OF THE INVENTION

Methods are provided for the manufacture of aromatics from oxygenate feeds.

BACKGROUND OF THE INVENTION

Conversion of methanol feeds to aromatic compounds is an industrially valuable reaction. Conventional methods for converting methanol to aromatics can involve exposing a methanol-containing feed to a molecular sieve, such as ZSM-5. In addition to forming aromatic compounds, some olefins can also be produced. Reactions for conversion of methanol can be useful, for example, for creation of aromatics and olefins as individual products, or for formation of aromatic and olefin mixtures for use as naphtha boiling range or distillate boiling range fuels.

One difficulty with methods for conversion of methanol to aromatics is that the conversion reaction can have a relatively low yield of aromatics. The low yields from conventional methods can pose a variety of challenges, such as requiring large equipment footprints relative to total product volume as well as loss of initial reactant to various side reactions.

U.S. Pat. Nos. 4,049,573 and 4,088,706 disclose conversion of methanol to a hydrocarbon mixture rich in $C_2$-$C_3$ olefins and mononuclear aromatics, particularly p-xylene, by contacting the methanol at a temperature of 250-700° C. and a pressure of 0.2 to 30 atmospheres with a crystalline aluminosilicate zeolite catalyst which has a Constraint Index of 1-12 and which has been modified by the addition of an oxide of boron or magnesium either alone or in combination or in further combination with oxide of phosphorus. The above-identified disclosures are incorporated herein by reference.

Methanol can be converted to gasoline employing the MTG (methanol to gasoline) process. The MTG process is disclosed in the patent art, including, for example, U.S. Pat. Nos. 3,894,103; 3,894,104; 3,894,107; 4,035,430 and 4,058,576. U.S. Pat. No. 3,894,102 discloses the conversion of synthesis gas to gasoline. MTG processes provide a simple means of converting syngas to high-quality gasoline. The ZSM-5 catalyst used is highly selective to gasoline under methanol conversion conditions, and is not known to produce distillate range fuels, because the $C_{10}$+ olefin precursors of the desired distillate are rapidly converted via hydrogen transfer to heavy polymethylaromatics and $C_4$ to $C_8$ isoparaffins under methanol conversion conditions.

Olefinic feedstocks can also be used for producing $C_5$+ gasoline, diesel fuel, etc. In addition to the basic work derived from ZSM-5 type zeolite catalysts, a number of discoveries contributed to the development of the industrial process known as Mobil Olefins to Gasoline/Distillate ("MOGD"). This process has significance as a safe, environmentally acceptable technique for utilizing feedstocks that contain lower olefins, especially $C_2$ to $C_5$ alkenes. In U.S. Pat. Nos. 3,960,978 and 4,021,502, Plank, Rosinski and Givens disclose conversion of $C_2$ to $C_5$ olefins alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over ZSM-5 is effective at moderately elevated temperatures and pressures. The conversion products are sought as liquid fuels, especially the $C_5$+ aliphatic and aromatic hydrocarbons. Olefinic gasoline is produced in good yield by the MOGD process and may be recovered as a product or recycled to the reactor system for further conversion to distillate-range products. Operating details for typical MOGD units are disclosed in U.S. Pat. Nos. 4,445,031; 4,456,779, Owen et al, and U.S. Pat. No. 4,433,185, Tabak, incorporated herein by reference.

In addition to their use as shape selective oligomerization catalysts, the medium pore ZSM-5 type catalysts are useful for converting methanol and other lower aliphatic alcohols or corresponding ethers to olefins. Particular interest has been directed to a catalytic process ("MTO") for converting low cost methanol to valuable hydrocarbons rich in ethene and $C_3$+ alkenes. Various processes are described in U.S. Pat. No. 3,894,107 (Batter et al), U.S. Pat. No. 3,928,483 (Chang et al), U.S. Pat. No. 4,025,571 (Lago), U.S. Pat. No. 4,423,274 (Daviduk et al) and U.S. Pat. No. 4,433,189 (Young), incorporated herein by reference. It is generally known that the MTO process can be optimized to produce a major fraction of $C_2$ to $C_4$ olefins. Prior process proposals have included a separation section to recover ethene and other gases from by-product water and $C_5$+ hydrocarbon liquids. The oligomerization process conditions which favor the production of $C_{10}$ to $C_{20}$ and higher aliphatics tend to convert only a small portion of ethene as compared to $C_3$+ olefins.

The methanol to olefin process (MTO) operates at high temperature and near 30 psig in order to obtain efficient conversion of the methanol to olefins. These process conditions, however, produce an undesirable amount of aromatics and $C_2$ olefins and require a large investment in plant equipment.

The olefins to gasoline and distillate process (MOGD) operates at moderate temperatures and elevated pressures to produce olefinic gasoline and distillate products. When the conventional MTO process effluent is used as a feed to the MOGD process, the aromatic hydrocarbons produced in the MTO unit are desirably separated and a relatively large volume of MTO product effluent has to be cooled and treated to separate a $C_2$-light gas stream, which is unreactive, except for ethene which is reactive to only a small degree, in the MOGD reactor, and the remaining hydrocarbon stream has to be pressurized to the substantially higher pressure used in the MOGD reactor.

U.S. Pat. No. 3,998,898 describes a method for manufacture of gasoline using an MTG style process. In U.S. Pat. No. 3,998,898, a potential gasoline including aromatic compounds is manufactured from a feed that contains two types of aliphatic compounds. The feed can contain aliphatic compounds corresponding to a) "difficultly convertible" compounds, such as carboxylic acids and short chain aldehydes, and b) "easily convertible" compounds, such as aliphatic alcohols, ketones, and aldehydes containing 3 or more carbons, with the mixture having sufficient "easily convertible" compounds to make up for a stoichiometric deficiency due to the presence of any carboxylic acids in the feed. The use of a mixture of a "difficultly convertible" compound and an "easily convertible" compound meeting the specified criteria is described as improving the yield of gasoline boiling range compounds at the expense of compounds having 4 carbons or less.

U.S. Pat. No. 7,820,867 describes a variation on the methods from U.S. Pat. No. 3,998,898. The '867 patent describes integration of a reaction for converting synthesis gas to methanol (or other oxygenates) with a methanol to gasoline reaction. In the integrated system, the "difficultly convertible" compounds can be introduced into the reaction stage for conversion of synthesis gas to methanol. The same definition for "difficultly convertible" compounds used in U.S. Pat. No. 3,998,898 is maintained in the '867 patent.

Despite numerous prior art processes, there is an ongoing desire to improve methods of converting methanol to aromatics that yield a higher amount of aromatics than the prior art methods. There is a particular interest in methods that produce high yields of paraxylene, considering paraxylene's value in industry and its use in the manufacture of terephthalic acid, an intermediate in the production of synthetic fibers.

SUMMARY OF THE INVENTION

The present invention provides methods for improving the yield of aromatics, particularly paraxylene, from conversion of oxygenate feeds including methanol. In one aspect, an oxygenate feed having an effective hydrogen index of about 1.4 to about 1.9 is exposed to an aromatization catalyst under effective conversion conditions to form a conversion effluent comprising one or more aromatic compounds. The oxygenate feed contains 5 wt. % or less of carbon-containing compounds different from CO and $CO_2$ that have a hydrogen index of 1 or less. Optionally, the oxygenate feed can be substantially free of carboxylic acids, such as a feed that comprises, consists essentially of, and/or consists of ketones, alcohols, $C_3+$ aldehydes, and combinations thereof.

In another aspect, methanol is reacted with a pyrolysis oil over an aromatization catalyst in a series of steps to form aromatics. The introduction of the pyrolysis oil is advantageously staged to reduce or minimize the coking and/or fouling effects of the reaction with pyrolysis oil. Thus, the total volume of the pyrolysis oil to be reacted is split into at least two portions, and each portion is fed, with an oxygenate feed (together "fresh feed"), to a reactor or series of reactors at a different location to react with an aromatization catalyst and the effluent from the previous step. Preferably, the volume percentage of pyrolysis oil in each successive fresh feed increases, but less fresh feed is introduced at downstream entry points as compared to the first entry point, and the total percentage of the pyrolysis oil in the total amount of fresh feed is greater than the volume percentage of the pyrolysis oil of the feed introduced at the first entry point.

In one embodiment in which a pyrolysis oil is used as a co-feed, a first feed comprising a first oxygenate feed having an effective hydrogen index of at least about 1 and a first portion of a pyrolysis oil feed is exposed to an aromatization catalyst at a first location under effective conversion conditions to form a first conversion effluent comprising one or more aromatic compounds. The volume percentage of the first portion of the pyrolysis oil feed is about 5 vol % to about 25 vol % of the volume of the first feed. At least a portion of the first conversion effluent, along with a second feed comprising a second oxygenate feed having an effective hydrogen index of at least about 1 and a second portion of the pyrolysis oil feed, is exposed to an aromatization catalyst at a second location under effective conversion conditions to form a second conversion effluent comprising one or more aromatic compounds. The volume of the second feed is less than the volume of the first feed, and the volume percentage of the first portion of the pyrolysis oil feed based on the total volume of the first and second feeds is greater than the volume percentage of the first portion of the pyrolysis oil feed. Optionally, at least a portion of the second conversion effluent, along with a third (or fourth, or fifth, etc.) feed comprising a third oxygenate feed having an effective hydrogen index of at least about 1 and a third portion of the pyrolysis oil feed, is exposed to an aromatization catalyst at a third location under effective conversion conditions to form a third conversion effluent comprising one or more aromatic compounds.

In still another embodiment, an oxygenate feed having an effective hydrogen index of at least about 1 and a pyrolysis oil feed is introduced into a conversion reaction system at a plurality of feed entry points. The reaction system has a direction of flow, and each of the plurality of feed entry points is located at a different location of the reaction system relative to the direction of flow. The plurality of feed entry points includes at least a first upstream entry point and a final downstream entry point. The portions of the oxygenate feed and the pyrolysis oil feed introduced at each of the plurality of feed entry points is exposed to at least a portion of an aromatization catalyst to form a plurality of converted effluents, and at least a portion of the converted effluents from upstream feed entry points are combined with the portions of the oxygenate feed and the pyrolysis oil feed introduced at a downstream feed entry point. The volume percentage of pyrolysis oil feed based on the total volume of the portions of the oxygenate feed and the pyrolysis oil feed is greater than the volume percentage of the portion of the pyrolysis oil feed introduced at the first upstream entry point. Optionally, the volume percentage of the portion of the pyrolysis oil at each feed entry point is greater than the volume percentage of the portion of the pyrolysis oil feed introduced at upstream feed entry points, the volume percentage of the portion of the pyrolysis oil feed being based on the total volume of the portions of the oxygenate feed and the pyrolysis oil feed introduced at the same entry point. Alternatively, the volume percentage of the portion of the pyrolysis oil feed introduced at least two feed entry points is substantially similar.

The aromatization catalyst utilized herein comprises a molecular sieve, preferably ZSM-5, and at least one Group 8-14 element. Effective conversion conditions for the methods provided are a pressure of about 100 kPaa to about 2500 kPaa, a temperature of about 300° C. to about 600° C., and a weight hourly space velocity of about 0.1 $hr^{-1}$ to about 20 $hr^{-1}$. The claimed methods and co-feeds provide an increased yield of aromatics as compared to methods using methanol alone.

DETAILED DESCRIPTION OF THE EMBODIMENTS

Overview

In various aspects, methods are provided for improving the yield of aromatics during conversion of oxygenate feeds. An oxygenate feed can contain a mixture of oxygenate compounds, including one or more compounds with a hydrogen index of less than 2, so that an effective hydrogen index of the mixture of oxygenates is between about 1.4 and 1.9. Optionally, the mixture of oxygenates can include one or more ketones or aldehydes having 3 or more carbons. Additionally or alternately, the mixture of oxygenates can exclude compounds having a hydrogen index of less than 1 and/or can exclude carboxylic acids, formaldehyde, and acetaldehyde. An example of a mixture of oxygenates having an effective hydrogen index of between about 1.4 and 1.9 can be a mixture of acetone, butanol (such as n-butanol), and ethanol. Such a mixture of oxygenates can also include methanol and/or dimethyl ether.

In other aspects, a mixture of oxygenates with an effective hydrogen index greater than about 1 can be converted with a pyrolysis oil co-feed. Pyrolysis oils are mixtures of oxygenates formed from pyrolysis of biomass in an atmosphere containing a reduced amount of oxygen. Pyrolysis oils can be difficult to process for various reasons, including an elevated content of oxygenates and aromatics as well as the presence of substantial amounts of carboxylic acids. However, the difficulties in co-processing a pyrolysis oil can be reduced or minimized by staging the introduction of pyrolysis oil into a reaction system. This can allow varying mixtures of pyrolysis oil and methanol (or another oxygenate feed) to be introduced into a reaction system at various feed entry points. This type of staged addition can allow for use of increased amounts of pyrolysis oil in the overall feed for a conversion process while reducing or minimizing problems in a reactor due to plugging or formation of coke.

Hydrogen Index and Effective Hydrogen Index

In various aspects, an improved feed for forming aromatic compounds can be provided by using a feed with an effective hydrogen index of less than 2, such as an effective hydrogen index of about 1.4 to about 1.9. The effective hydrogen index (EHI) of a feed can be calculated based on the hydrogen index values of the components of a feed. In this discussion, a reference to a hydrogen index or hydrogen index value corresponds to a value for a single compound, while an effective hydrogen index represents a value for a feed containing one or more components.

The hydrogen index (HI) of a compound containing only carbon, hydrogen, and oxygen can be expressed as HI=[n−2p]/m, where m, n, and p refer to the stoichiometric values in a chemical formula expressed as $C_mH_nO_p$. Based on this definition, examples of hydrogen index values for oxygenate compounds are: aliphatic alcohols have a hydrogen index of 2; acetone and propanal have a hydrogen index of 1.33 (C4+ ketones and aldehydes have HI values between 1.5 and 2); acetaldehyde has a hydrogen index of 1; aromatic oxygenates (such as phenols) have hydrogen index values less than 1; and formaldehyde and sugars have a hydrogen index of 0. Carboxylic acids have a wide range of HI values, ranging from −1 for formic acid to greater than 1 for C5+ carboxylic acids. It is noted that benzene has an HI value of 1, while C7+ single ring aromatic hydrocarbons have HI values slightly greater than 1. After determining the hydrogen index values for the components in a feed, the effective hydrogen index for the feed can be determined based on a mole weighted average of the hydrogen index values of the individual components.

Mixtures of Oxygenates with Hydrogen Index of at Least 1

Hydrogen index can assist in characterizing a feed for conversion of oxygenates to aromatics. For example, the formula for methanol (HI=2) is $CH_4O$. During a conversion reaction, the oxygen in the methanol typically forms water. After removing a water unit, the remaining atoms in methanol correspond to a $CH_2$ unit. In order to form a $C_6$ aromatic compound (HI=1) from $CH_2$ units (HI=2), 6 additional hydrogen atoms (or 3 $H_2$ molecules) have to be accounted for, such as by reaction with other compounds. In other words, for an oxygenate to aromatics conversion reaction, a comparison of the hydrogen index for feed and products indicates the amount of excess hydrogen atoms that have to be accounted for. In a reaction environment for forming aromatics from methanol (or other oxygenates), these additional hydrogens have to be incorporated into other products from the conversion reaction. Conventionally, the additional hydrogen atoms are accounted for by forming short chain aliphatic compounds, such as ethane and propane, which have a stoichiometry of $C_nH_{2n+2}$. Based on stoichiometry, in an idealized reaction for forming benzene from methanol, this means at least three alkanes (ethane) have to be formed for each aromatic formed. This can result in a substantial reduction in the yield of aromatics from the conversion process, as at least as many carbon atoms have to be incorporated into alkane products as are incorporated into aromatic products.

Instead of forming substantial amounts of alkanes, the additional $H_2$ units can be consumed by hydrogenating compounds (such as oxygenate compounds) with lower HI values. For example, formaldehyde has an HI value of 0. From a stoichiometry standpoint, 3 methanols plus 3 formaldehydes can be used to form a C6 aromatic without requiring formation of additional alkanes. More generally, any compounds present within a feed can potentially react with the excess hydrogen, including compounds that are not directly involved with formation of aromatic compounds.

Under conventional methods, such as the methods in U.S. Pat. No. 7,820,867, increasing the yield of aromatics from an oxygenate feed was believed to require mixing of "easily convertible" compounds (having HI values greater than 1) with "difficultly convertible" compounds having HI values less than 1. In such conventional methods, ketones and C3+ aldehydes were considered "easily convertible" compounds, while all carboxylic acids were defined as "difficultly convertible" regardless of HI value. However, it has been unexpectedly determined that the yield of aromatics can be improved using mixtures of oxygenates to form a feed having an effective hydrogen index of 1.4 to 1.9, where substantially all of the oxygenates in the feed have an HI value of greater than 1. Preferably, substantially none of the oxygenates in the feed are carboxylic acids. An example of such an oxygenate feed can be a feed composed of alcohols, ketones, and $C_3+$ aldehydes that have a hydrogen index of greater than 1. In such a feed, substantially all of the components in the feed can represent compounds that are conventionally believed to be "easily convertible" compounds. However, an improved yield of aromatics relative to feed with an EHI value of 2 (i.e., a feed of alcohols and/or dialkyl ethers) can still be obtained. A feed with substantially all components being "easily convertible" is defined herein as a feed containing about 5 wt. % or less of components that have a hydrogen index less than 1 and/or that are carboxylic acids. For example, a feed with substantially all components being easily convertible can contain about 3 wt. % or less of components that have a hydrogen index less than 1 and/or that are carboxylic acids, or about 1 wt. % or less, or about 0.5 wt. % or less, or about 0.1 wt. % or less.

One example of a feed that can have substantially all components that are "easily convertible" compounds is a mixture of acetone, butanol (preferably n-butanol), and ethanol. Mixtures of acetone, n-butanol, and ethanol are an example of a type of fermentation product that can be formed from fermentation of starch by some biological processes. A typical yield from such a fermentation process (on a dry basis) can be about 30 vol % acetone, about 60 vol % n-butanol, and about 10 wt. % ethanol in the product. This type of mixture of acetone, n-butanol, and ethanol can be not only suitable for use in synthesis of aromatics, but can in fact provide an improved yield relative to a pure alcohol feed. More generally, a variety of biological processes (such as fermentation processes) can produce mixtures of alcohols and ethers that also include ketones and $C_3+$ aldehydes. Such mixtures can have an EHI of less than about 1.9, thus allowing for use of the mixtures for conversion to aromatics with an improved yield of aromatics relative to a feed with an EHI of 2.

Mixtures of Oxygenates with Pyrolysis Oils (Staged Addition)

Another option for providing a process with improved aromatics yield can be to use a traditionally lower value stream as a source of compounds with low hydrogen index. Pyrolysis oils are an example of a potential feed stream containing low hydrogen index compounds. Pyrolysis oils can include a large variety of oxygenate and/or aromatic compounds, and the composition of pyrolysis oils can vary depending on the nature of the original feed and the pyrolysis conditions. From an effective hydrogen index standpoint, pyrolysis oils are a potentially useful co-feed for an oxygenate conversion process, as typical pyrolysis oils can have an effective hydrogen index of less than 1. However, pyrolysis oils are conventionally viewed as less desirable for use as a co-feed during conversion of oxygenates to aromatics due to an increased tendency for pyrolysis oils to coke and/or foul the conversion reactor. This coking is believed to increase with increasing concentrations of pyrolysis oil in a feed for conversion.

Figure 3:
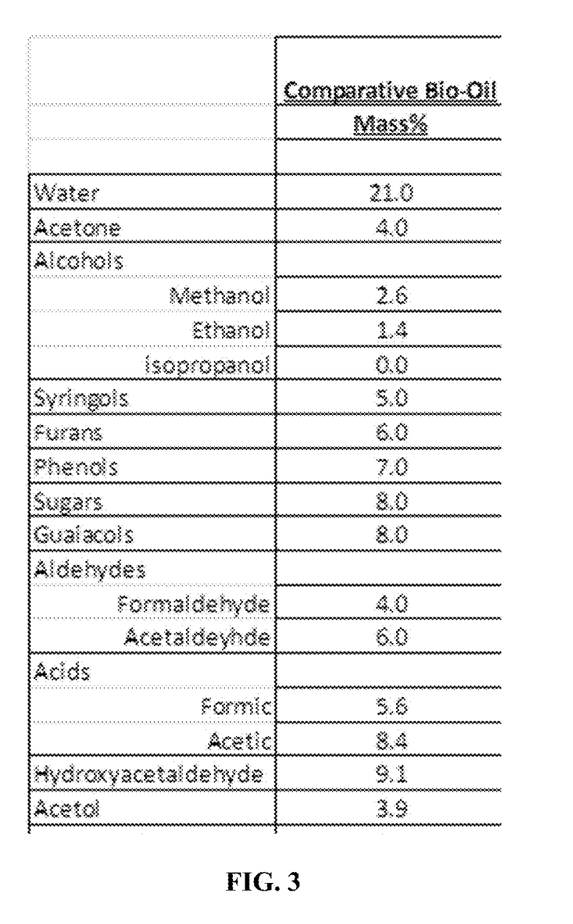
FIG. 3 shows an example of a bio-oil composition.

An illustrative example of a possible pyrolysis oil composition is shown in FIG. 3. The composition in FIG. 3 was described in "Exploratory Studies of Fast Pyrolysis Oil Upgrading", F. H. Mahfud, Rijksuniversiteit Groningen, Nov. 16, 2007, ISBN 978-90-367-3226-9.

As shown in FIG. 3, a pyrolysis oil can contain a substantial portion of aromatic compounds, such as syringols, furans, phenols, and guaiacols. Due in part to the presence of the aromatic compounds, incorporating pyrolysis oils into a feed for an oxygenate conversion process is conventionally believed to lead to substantial coking of the catalyst. This coking can foul a conversion reactor and potentially prevent operation of the reactor at higher concentrations of pyrolysis oil in a feed.

In various aspects, the difficulties with coking in a conversion reactor when using a pyrolysis oil as a co-feed can be reduced or minimized by staging the addition of the pyrolysis oil in a reaction system by using a plurality of feed entry points. For example, in a reaction system using a series of reactors (or alternatively a series of feed entry points within a single reactor), the ratio of methanol (or another high EHI feed) to pyrolysis oil can be set separately for each reactor and/or feed entry point. The ratio of methanol to pyrolysis oil in the first reactor can be set to a relatively low value, so that 25 vol % or less of the feed corresponds to pyrolysis oil. This can reduce or minimize the coking in the initial reactor. The feed to the second reactor can then correspond to the effluent from the first reactor plus an additional amount of both the methanol and the pyrolysis oil. Based on the presence of the effluent from the first reactor, a higher percentage of the fresh feed in the second reactor (feed entry point) can correspond to the pyrolysis oil. In an example using three feed entry points, the volume percentage of pyrolysis oil in the fresh feed to the second reactor can be at about 25 vol % to about 70 vol %, or about 25 vol % to about 50 vol %. The effluent from the second reactor can then be used as a portion of the feed to a third reactor. The fresh feed to the third reactor can include a still larger percentage of pyrolysis oil, such as about 40 vol % to about 80 vol %.

More generally, staging of addition of the pyrolysis oil in the feed to the conversion reaction can be used with any convenient reaction system configuration. The concept of staging is based on introducing a total feed to a reaction system by splitting the feed across multiple feed entry points at different locations relative to the direction of flow within the reaction system. Additionally, the composition of the feed at each feed entry point will typically be different from the total composition for the feed. The staging can be performed by using multiple reactors, with different concentrations of pyrolysis oil in the feed to each reactor. Additionally or alternately, the staging can be performed by introducing feed in multiple locations (feed entry points) in a reactor, with downstream locations in the reactor receiving greater percentages of pyrolysis oil in the feed. The staging of addition of the feed can be used with fixed bed reactors, fluidized bed reactors, moving bed reactors, or any other convenient type of reactor. In some preferred aspects, the reactors used can be fluidized bed reactors or other reactors that can facilitate regeneration and recycle of catalyst within the reactor.

In this discussion, references to introducing a feed or a co-feed at a feed entry point are understood as including any convenient method for introducing a feed. For example, a high EHI feed (such as a methanol feed) and a pyrolysis oil feed can be mixed prior to entering a reaction system via a feed entry point, or the high EHI feed and the pyrolysis oil feed can be introduced into a reaction system separately at similar locations relative to the direction of flow within the reaction system.

The number of feed entry points in a reaction system having staged (different) amounts of pyrolysis oil in the fresh feed can be any convenient number. At least two different feed entry points are needed in order to have staged addition of the pyrolysis oil. In various aspects, introducing the pyrolysis oil co-feed using three to eight feed points having different concentrations can be preferred. In order to avoid fouling, the highest pyrolysis oil volume percentage (concentration) at any feed entry point can be about 80 vol % or less.

When using multiple feed entry points for a feed including a pyrolysis oil, higher amounts of pyrolysis oil can be introduced into the later (downstream) feed entry points. Preferably, the amount of feed introduced into a reaction system at all prior upstream feed entry points can be at least as great as the amount of feed introduced at any single downstream feed entry point. This can assist with providing a sufficient volume of previously reacted feed so that production of coke due to downstream introduction of pyrolysis oil is reduced or minimized.

In various aspects, the combined amount of feed (high EHI feed plus pyrolysis oil feed) introduced at the first entry point can be at least 20 vol % of the total amount of feed (high EHI feed plus pyrolysis oil feed) introduced into the conversion reaction system, such as at least about 25 vol %, or at least about 30 vol %, or at least about 35 vol %. Additionally or alternately, the combined amount of feed introduced at the first entry point can be about 75 vol % or less of the total amount of feed introduced into the conversion reaction system, such as about 65 vol % or less, or about 50 vol % or less. In some aspects, after the initial feed entry point, the combined amount of feed introduced at each subsequent feed entry point can preferably be at least about 5 vol % of the total amount of feed introduced into the conversion reaction system, or at least about 10 vol %. By staging the introduction of the pyrolysis oil, the net concentration of pyrolysis oil in the total feed across all feed entry points can be as high as 70 vol %, such as about 15 vol % to about 70 vol %, preferably about 25 vol % to about 70 vol %, and most preferably 50 vol % to 70 vol % of the feed.

In some alternative aspects, a single feed entry point can be used for introduction of a pyrolysis oil co-feed. In such aspects, the amount of pyrolysis oil used as a co-feed can be about 5 vol % to about 50 vol %, preferably about 10 vol % to about 40 vol %, and more preferably about 15 vol % to about 30 vol %.

For a reaction system with a plurality of feed entry points, such as two to eight feed entry points, or three to eight feed entry points, the pyrolysis oil concentration can vary at each feed entry point. For the first or initial feed entry point, the pyrolysis oil concentration can be from 5 vol % to 25 vol % relative to the total weight of feed introduced at the first feed entry point, preferably from 10 vol % to 25 vol %, and more preferably from 15 vol % to 20 vol %. For the final feed entry point, the pyrolysis oil concentration can be from about 30 vol % to about 80 vol %, preferably about 40 vol % to about 80 vol %, more preferably about 40 vol % to about 70 vol %, and even more preferably about 50 vol % to about 70 vol %. If three or more feed entry points are used, in some aspects at least one intermediate feed entry point can have a pyrolysis oil concentration of about 25 vol % to about 50 vol %, preferably about 25 vol % to about 45 vol %, and more preferably about 30 vol % to about 40 vol %. Additionally or alternately, if three or more feed entry points are used, in some aspects at least one intermediate feed entry point can have a pyrolysis oil concentration of about 35 vol % to about 60 vol %, preferably about 40 vol % to about 60 vol %, and more preferably 40 vol % to about 55 vol %.

In some aspects, two or more of the feed entry points can have a substantially similar concentration of pyrolysis oil. In other aspects, each subsequent feed entry point can have a higher concentration of pyrolysis oil than the prior feed entry point, such as at least 5 vol % greater, or at least 10 vol % greater. Any convenient method or scheme can be used for varying the relative amounts of high EHI feed and pyrolysis oil feed at the various feed entry points. For example, one option can be to introduce the same amount of pyrolysis oil at each feed entry point while varying the amount of methanol (or other high EHI feed) at the feed entry points to achieve the desired variation in pyrolysis oil concentration. Another option can be to introduce the same total weight of feed at each feed entry point while varying the amounts of high EHI feed and pyrolysis oil feed.

By using staged addition of pyrolysis oil, an increased amount of pyrolysis oil can be used as a co-feed for conversion of oxygenates to aromatics while reducing or minimizing the amount of additional coke formed in the reaction system. For the first reactor and/or first feed entry stage of the reaction system, the amount of coke generated in the reactor can roughly correspond to the amount of coke expected based on the percentage of pyrolysis oil in the feed. However, for a second (or other subsequent) addition locations for the feed, the amount of coke can correspond to an amount less than would be expected based on addition of all of the pyrolysis oil with the initial feed. Instead, the effluent from the earlier reactors (or upstream locations) can act as a diluent so that the amount of coke generated is comparable to what would be expected based on the concentration of the fresh pyrolysis oil in the total input flow to a given reactor stage or location. It is also noted that using staged addition of the pyrolysis oil can reduce or minimize the amount of methanol that is consumed in alkylation of the pyrolysis oil instead of being converted to the desired aromatic compounds.

Figure 1:
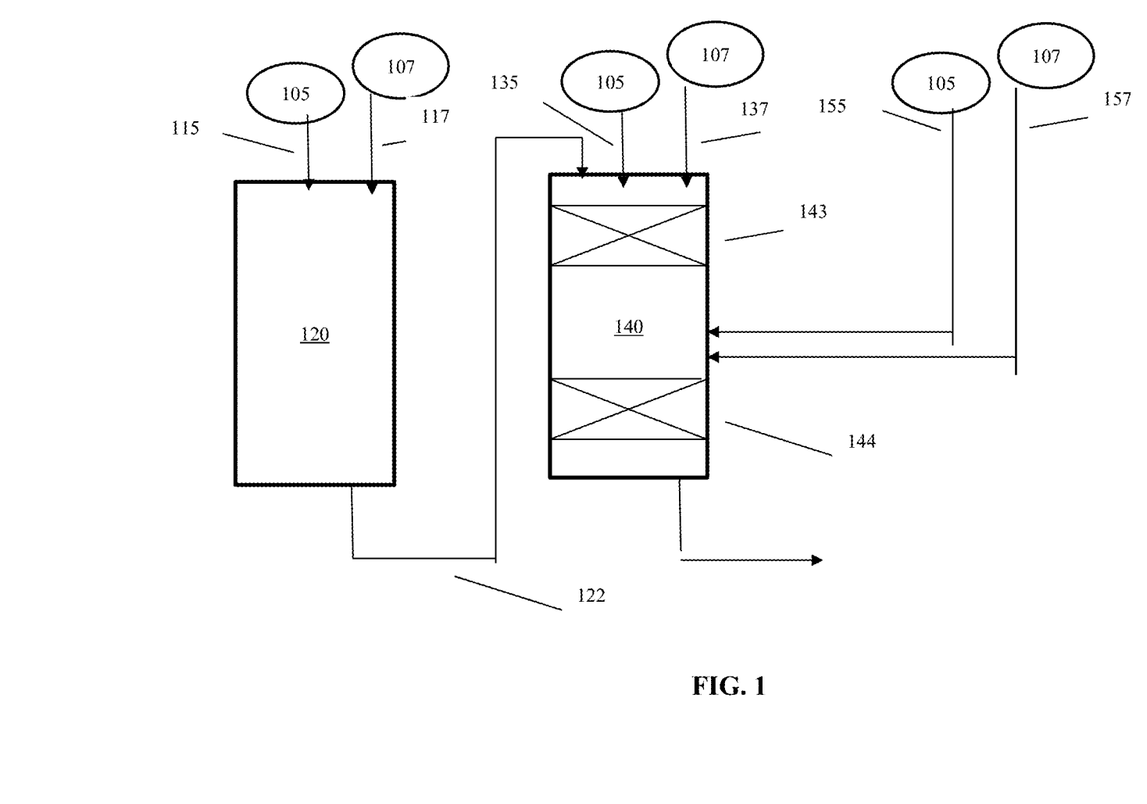
FIG. 1 schematically shows an example of a reaction system having multiple feed entry points for converting an oxygenate feed to form aromatics.

FIG. 1 schematically shows an example of a reaction system suitable for introducing pyrolysis oil in a stage manner during an oxygenate to aromatics conversion process. For convenience in illustrating the concept, FIG. 1 shows examples of both using multiple reactors for staged addition as well as introducing feeds at multiple locations within a reactor. Of course, any convenient combination of additional reactors and additional feed entry points can be used, such a reaction system using separate reactors for each feed entry point and/or a reaction system comprising a single reactor with multiple feed entry points. The reactors in FIG. 1 can correspond to any convenient type of reactor for stage addition of feed. For convenience, the reactors in FIG. 1 are shown as fixed bed reactors, but fluidized bed reactors or riser reactors could also be used.

In FIG. 1, two sources of feed for the reaction system are shown. One feed source 105 of feed is a feed with an effective hydrogen index greater than 1, such as a feed comprising methanol and/or dimethyl ether, or a feed comprising a mixture of alcohols and ethers. A second feed source 107 can provide a pyrolysis oil feed to the reaction system. FIG. 1 shows these feed sources schematically as corresponding to multiple instances of feed sources for convenience. In other aspects, a single high hydrogen index feed source 105 and/or pyrolysis oil feed source 107 could be used. FIG. 1 also depicts introducing feed streams derived from feed source(s) 105 and 107 as separate feed streams into a reaction system at various feed entry locations. Of course, a feed stream comprising a mixture of feeds from a feed source 105 and a feed source 107 can be mixed together prior to entering a reactor. Mixing a pyrolysis oil with a methanol (or other high effective hydrogen index stream) could be beneficial, for example, to provide better mixing prior to entering a reactor or to improve the flow properties of the pyrolysis oil feed for delivery to a reaction system.

In FIG. 1, feed streams 115 and 117 (from feed sources 105 and 107, respectively) are delivered to a first conversion reactor 120. Second conversion reactor 140 similarly receives feed streams 135 and 137, along with first conversion reactor effluent 122. The feed streams 135 and 137, along with first conversion reactor effluent 122, are introduced into second conversion reactor 140 prior to an initial catalyst bed 143. Feed streams 155 and 157 are introduced into reactor 140 between initial catalyst bed 143 and final catalyst bed 144. At the location where feed streams 155 and 157 are introduced, the feed streams are at least partially mixed with effluent from initial catalyst bed 143 prior to passing through final catalyst bed 144.

For a configuration such as the reaction system shown in FIG. 1, the relative amounts of feed from feed sources 105 and 107 at each feed entry location can be varied so that the percentage of feed from feed source 107 increases at later feed entry locations. For example, for a combined amount of feed delivered to the first conversion reactor 120, 80 vol % of the feed can correspond to feed stream 115 from source 105, while 20 vol % can correspond to feed stream 117 from source 107. At the second feed entry location, 50 vol % of the fresh feed can be in feed stream 135 while the other 50 vol % can be in feed stream 137. At the third (final) feed entry location, 30 vol % of the fresh feed can be in feed stream 155 while the remaining 70 vol % can be in feed stream 157.

Conversion Conditions

One option for performing an oxygenate to aromatics conversion reaction, such as a methanol to gasoline type process, can be to use a moving or fluid catalyst bed with continuous oxidative regeneration. The extent of coke loading on the catalyst can then be continuously controlled by varying the severity and/or the frequency of regeneration. In a turbulent fluidized catalyst bed the conversion reactions are conducted in a vertical reactor column by passing hot reactant vapor upwardly through the reaction zone at a velocity greater than dense bed transition velocity and less than transport velocity for the average catalyst particle. A continuous process is operated by withdrawing a portion of coked catalyst from the reaction zone, oxidatively regenerating the withdrawn catalyst and returning regenerated catalyst to the reaction zone at a rate to control catalyst activity and reaction severity to effect feedstock conversion. Preferred fluid bed reactor systems are described in Avidan et al. (U.S. Pat. No. 4,547,616); Harandi et al. (U.S. Pat. No. 4,751,338); and Tabak et al. (U.S. Pat. No. 4,579,999), each of which is incorporated herein by reference in its entirety. In other aspects, other types of reactors can be used, such as fixed bed reactors, riser reactors, fluid bed reactors, and/or moving bed reactors.

A suitable feed can be converted to aromatics by exposing the feed to an aromatization catalyst under effective conversion conditions. General conversion conditions include a pressure of about 100 kPaa to about 2500 kPaa, preferably about 100 kPaa to about 2000 kPaa, more preferably about 100 kPaa to about 1500 kPaa, and ideally about 100 kPaa to about 1200 kPaa. The amount of feed (weight) relative to the amount of catalyst (weight) can be expressed as a weight hourly space velocity (WHSV). Suitable weight hourly space velocities include a WHSV of about 0.1 hr$^{-1}$ to about 20 hr$^{-1}$, preferably about 1.0 hr$^{-1}$ to about 10 hr$^{-1}$. A wide range of temperatures can be suitable, depending on the desired type of aromatics-containing product. Thus, temperatures of about 300° C. to about 600° C., preferably about 300° C. to about 500° C., and more preferably about 350° C. to about 450° C.

Aromatization Catalyst

The catalyst used herein is a composition of matter comprising a molecular sieve and a Group 8-14 element, or combination of metals from the same group of the Periodic Table. The composition of matter can optionally further comprise phosphorus and/or lanthanum and/or other elements from Group 1-2 and/or Group 13-16 of the Periodic Table that provide structural stabilization. In this sense, the term "comprising" can also mean that the catalyst can comprise the physical or chemical reaction product of the molecular sieve and the Group 8-14 element or combination of elements from the same group (and optionally phosphorus and/or lanthanum and/or other elements from groups 1-2 and/or group 13-16). In this description, reference to a group number for an element corresponds to the current IUPAC numbering scheme for the periodic table. Optionally, the catalyst may also include a filler or binder and may be combined with a carrier to form slurry.

In various aspects, the molecular sieve comprises ≥10.0 wt. % of the catalyst, such about 10.0 to 100.0 wt. %, preferably about 25.0 to 95.0 wt. %, and more preferably about 50.0 to 90.0 wt. %.

As used herein the term "molecular sieve" refers to crystalline or non-crystalline materials having a porous structure. Microporous molecular sieves typically have pores having a diameter of ≤about 2.0 nm. Mesoporous molecular sieves typically have pores with diameters of about 2 to about 50 nm. Macroporous molecular sieves have pore diameters of >50.0 nm.

Particular molecular sieves are zeolitic materials. Zeolitic materials are crystalline or para-crystalline materials. Some zeolites are aluminosilicates comprising [SiO4] and [AlO4] units. Other zeolites are aluminophosphates (AlPO) having structures comprising [AlO4] and [PO4] units. Still other zeolites are silicoaluminophosphates (SAPO) comprising [SiO4], [AlO4], and [PO4] units.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18, AlPO-34 and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof.

Additionally or alternatively, the molecular sieves useful herein may be characterized by a ratio of Si to Al. In particular embodiments, the molecular sieves suitable herein include those having a Si/Al ratio of about 0.05 to 0.5.

In an embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496, published Apr. 16, 1998, both of which are herein fully incorporated by reference.

Particular molecular sieves useful in this invention include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-34 (U.S. Pat. No. 4,079,095) ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). The entire contents of the above references are incorporated by reference herein. Other useful molecular sieves include MCM-22, PSH-3, SSZ-25, MCM-36, MCM-49 or MCM-56, with MCM-22. Still other molecular sieves include Zeolite T, ZK5, erionite, and chabazite.

Another option for characterizing a zeolite (or other molecular sieve) is based on the nature of the ring channels in the zeolite. The ring channels in a zeolite can be defined based on the number of atoms included in the ring structure that forms the channel. In some aspects, a zeolite can include at least one ring channel based on a 10-member ring. In such aspects, the zeolite preferably does not have any ring channels based on a ring larger than a 10-member ring. Examples of suitable framework structures having a 10-member ring channel but not having a larger size ring channel include EUO, FER, IMF, LAU, MEL, MFI, MFS, MTT, MWW, NES, PON, SFG, STF, STI, TON, TUN, MRE, and PON.

In some aspects, the catalyst can also optionally include at least one metal selected from Group 8-14 of the Periodic Table, such as at least two metals (i.e., bimetallic) or at least three metals (i.e., trimetallic). Typically, the total weight of the Group 8-14 elements is from about 0.1 to 10 wt. % based on the total weight of the catalyst, preferably from about 0.1 to 2.0 wt. %, and more preferably from about 0.1 to 1.0 wt. %. Of course, the total weight of the Group 8-14 elements shall not include amounts attributable to the molecular sieve itself.

Additionally or alternatively, in some aspects, the catalyst can also include at least one of phosphorous and/or lanthanum and/or other elements from groups 1-2 and/or group 13-16, such as at least two such elements or at least three such elements. Typically, the total weight of the phosphorous and/or lanthanum and/or other elements from groups 1-2 and/or groups 13-16 is about 0.1 to 1.0 wt. % based on the total weight of the catalyst. Of course, the total weight of the phosphorous and/or lanthanum and/or other elements from groups 1-2 and/or groups 13-16 shall not include amounts attributable to the molecular sieve itself.

For the purposes of this description and claims, the numbering scheme for the Periodic Table Groups corresponds to the current IUPAC numbering scheme. Therefore, a "Group 4 metal" is an element from Group 4 of the Periodic Table, e.g., Hf, Ti, or Zr. The more preferred molecular sieves are SAPO molecular sieves, and metal-substituted SAPO molecular sieves. In particular embodiments, one or more Group 1 elements (e.g., Li, Na, K, Rb, Cs, Fr) and/or Group 2 elements (e.g., Be, Mg, Ca, Sr, Ba, and Ra) and/or phosphorous and/or Lanthanum may be used. One or more Group 7-9 element (e.g., Mn, Tc, Re, Fe, Ru, Os, Co, Rh, and Ir) may also be used. Group 10 elements (Ni, Pd, and Pt) are less commonly used in applications for forming olefins and aromatics, as the combination of a Group 10 element in the presence of hydrogen can tend to result in saturation of aromatics and/or olefins. In some embodiments, one or more Group 11 and/or Group 12 elements (e.g., Cu, Ag, Au, Zn, and Cd) may be used. In still other embodiments, one or more Group 13 elements (B, Al, Ga, In, and Tl) and/or Group 14 elements (Si, Ge, Sn, Pb) may be used. In a preferred embodiment, the metal is selected from the group consisting of Zn, Ga, Cd, Ag, Cu, P, La, or combinations thereof. In another preferred embodiment, the metal is Zn, Ga, Ag, or a combination thereof.

Particular molecular sieves and Group 2-13-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (E1APSO where E1 is Be, B, Cr, Co, Ga, Fe, Mg, Mn, Ti, or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti, or Zn), U.S. Pat. No. 4,310,440 (AlPO4), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326, and 5,478,787 (MgAPSO), U.S. Pat. No. 4,554,143 (FeAPO), U.S. Pat. Nos. 4,686,092, 4,846,956, and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617, and 4,880,520 (TiAPSO), U.S. Pat. Nos. 4,500,651, 4,551,236, and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066, and 5,675,050, all of which are herein fully incorporated by reference. Other molecular sieves include those described in R. Szostak, Handbook of Molecular Sieves, Van Nostrand Reinhold, New York, N.Y. (1992), which is herein fully incorporated by reference. In some aspects, the molecular sieve as modified by the Group 8-14 element and/or a Group 1-2, Group 13-16, lanthanum, and/or phosphorous is a ZSM-5 based molecular sieve.

Various methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), International Patent Application WO 01/36329 published May 25, 2001 (surfactant synthesis), International Patent Application WO 01/25151 published Apr. 12, 2001 (staged acid addition), International Patent Application WO 01/60746 published Aug. 23, 2001 (silicon oil), U.S. Patent Application Publication No. 2002-0055433 published May 9, 2002 (cooling molecular sieve), U.S. Pat. No. 6,448,197 (metal impregnation including copper), U.S. Pat. No. 6,521,562 (conductive microfilter), and U.S. Patent Application Publication No. 2002-0115897 published Aug. 22, 2002 (freeze drying the molecular sieve), which are all herein incorporated by reference in their entirety.

Example—Improved Aromatics Yield Using Easily Convertible Oxygenates

Four different oxygenate feeds were used as feeds for an oxygenate to aromatic conversion reaction. A first feed (diamond symbols in FIG. 2) was a conventional methanol (100%) feed with an effective hydrogen index of 2. A second feed (triangle symbols in FIG. 2) was a mixture of about 70 vol % methanol and about 30 vol % acetone with an effective hydrogen index of about 1.8. A third feed (circle symbols in FIG. 2) was a mixture of about 30 vol % acetone, about 55 vol % n-butanol, about 10 vol % ethanol, and about 5 vol % water, which also had an effective hydrogen index of about 1.8. This feed is believed to be representative of a type of acetone/n-butanol/ethanol mixture that could be generated from a suitable fermentation process. The fourth feed (square symbols in FIG. 2) was a mixture of about 55 vol % acetone, about 30 vol % n-butanol, about 10 vol % ethanol, and about 5 vol % water, resulting in an effective hydrogen index of between about 1.5 and 1.6. In the feeds with effective hydrogen index of between 1.4 and 1.9, all of the feed components have a hydrogen index of greater than 1.

The feeds were exposed to one of two types of aromatization catalysts under effective conditions for conversion of oxygenates to aromatics. The conditions included a temperature of about 450° C., a weight hourly space velocity of about 2 hr$^{-1}$, and a pressure of about 15 psig (about 100 kPag). At the conversion conditions, between 90 wt. % and 100 wt. % of each feed was converted. One aromatization catalyst used for performing the conversion reaction was a phosphorous stabilized ZSM-5 catalyst. The phosphorous content on the catalyst was about 1.2 wt. % relative to the total weight of the catalyst. The other aromatization catalyst was a ZSM-5 catalyst with 1 wt. % of Zn deposited on the catalyst.

Figure 2:
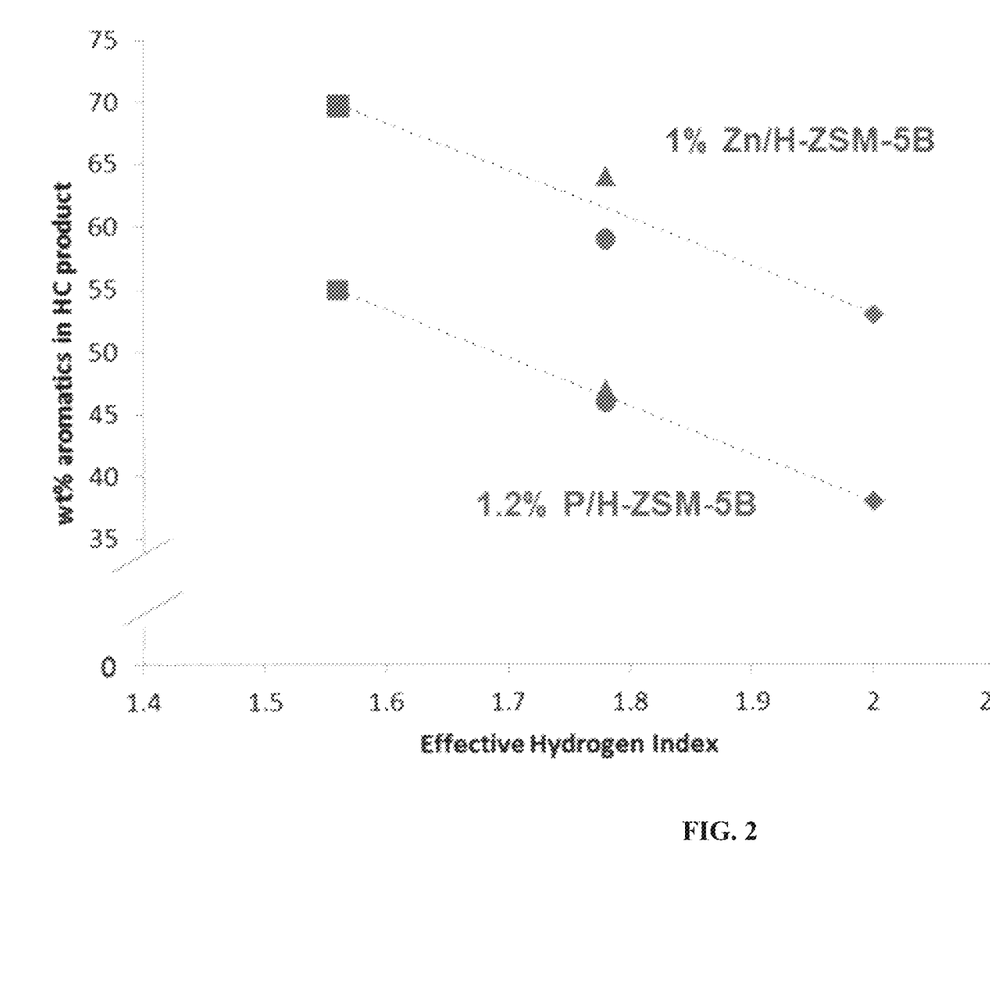
FIG. 2 shows results from converting feeds with various effective hydrogen index values to form aromatics.

FIG. 2 shows aromatic selectivities for the products generated from converting each of the four feeds in the presence of the two types of aromatization catalysts. In the results shown in FIG. 2, the Zn-ZSM-5 catalyst had generally higher aromatics production, but the same trend of dependence of aromatic selectivity on the feed was present for both catalysts. As shown in FIG. 2, using a mixture of oxygenates with an effective hydrogen index of less than 1.9 resulted in improved aromatics selectivity (yield) relative to a conventional 100% methanol feed. Altering the mixture of oxygenates at the same feed effective hydrogen index did not appear to alter the aromatics selectivity. Additionally, it is noted that further reducing the effective hydrogen index from about 1.8 to between about 1.5 and 1.6 resulted in still further increases in aromatics yield. This demonstrates that improvements in aromatics yield can be obtained from oxygenate mixtures that are conventionally believed to correspond to only "easily convertible" compounds.

Example—Improved Aromatics Yield with Pyrolysis Oil Co-Feed

A feed containing methanol and a feed including about 80 vol % methanol and 20 vol % pyrolysis oil were exposed to a fixed bed of an aromatization catalyst (ZSM-5) under effective conditions for conversion of oxygenates to aromatics. The weight hourly space velocity was about 6 hr$^{-1}$ and the pressure was about 1 atm (100 kPag). The conversion was performed at both 400° C. and 500° C. The conversion conditions were effective for substantially complete conversion of oxygenate compounds in the feeds.

At 400° C., conversion of the methanol feed resulted in a hydrocarbon product where 17.2 wt. % of the products were $C_6$-$C_9$ aromatics. Using the feed with 80 vol % methanol and 20 vol % pyrolysis oil, performing a conversion at 400° C. resulted in a hydrocarbon product where 26.4 wt. % of the products were $C_6$-$C_9$ aromatics. Similar results were observed at a conversion temperature of 500° C. Conversion of the methanol feed at 500° C. resulted in a hydrocarbon product with 19.4 wt. % $C_6$-$C_9$ aromatics, while conversion of the methanol/pyrolysis oil feed resulted in 26 wt. % $C_6$-$C_9$ aromatics. It is noted that attempting to process just the pyrolysis oil feed under the conversion conditions resulting in plugging of the catalyst bed.

In addition to improving the yield of aromatics, the co-processing of the methanol and pyrolysis feed also resulted in conversion of substantially all of the oxygenates in the pyrolysis oil into hydrocarbons. After separation of any desirable portions of the conversion effluent, such as a desired aromatics and/or naphtha fraction, another valuable portion of the effluent can be an upgraded pyrolysis oil that is more suitable for further processing in conventional refinery processes.

This example demonstrates the benefits of co-processing a pyrolysis oil feed with a high EHI oxygenate feed for aromatics production (such as gasoline production). By staging the addition of pyrolysis oil to a reaction system as described herein, the benefits of co-processing of pyrolysis oil can be achieved while reducing or minimizing the amount of coke production and/or fouling in the reaction system.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of the invention. Ranges disclosed herein include combinations of any of the enumerated values.

What is claimed is:

1. A method for converting oxygenates to aromatics, comprising:
   exposing a first feed comprising a first oxygenate feed comprising methanol and having an effective hydrogen index of at least about 1 and a first portion of a pyrolysis oil feed to an aromatization catalyst at a first location under effective conversion conditions to react methanol in the first oxygenate feed with pyrolysis oil in the first portion of the pyrolysis oil feed to form a first conversion effluent comprising one or more aromatic compounds, the volume percentage of the first portion of the pyrolysis oil feed being about 5 vol % to about 25 vol % of the volume of the first feed;
   exposing at least a portion of the first conversion effluent and a second feed comprising a second oxygenate feed comprising methanol and having an effective hydrogen index of at least about 1 and a second portion of the pyrolysis oil feed to the aromatization catalyst under effective conversion conditions to react methanol in the second oxygenate feed with pyrolysis oil in the second portion of the pyrolysis oil feed to form a second conversion effluent comprising one or more aromatic compounds, the volume of the second feed being less than the volume of the first feed;
   wherein the volume percentage of the first and second portions of the pyrolysis oil feed based on the total volume of the first and second feeds is greater than the volume percentage of the first portion of the pyrolysis oil feed in the first feed, and
   wherein said aromatization catalyst comprises ZSM-5 and at least one metal from Groups 8-14 of the Periodic Table.

2. The method of claim 1, further comprising exposing at least a portion of the second conversion effluent and a third feed comprising a third oxygenate feed having an effective hydrogen index of at least about 1 and a third portion of the pyrolysis oil feed to the aromatization catalyst under effective conversion conditions to form a third conversion effluent comprising one or more aromatic compounds, the volume of the third feed being less than the volume of the second feed.

3. The method of claim 1, wherein the volume percentage of the second portion of the pyrolysis oil feed is about 25 vol % to about 70 vol % of the volume of the second feed.

4. The method of claim 1, wherein the total volume percentage of pyrolysis oil feed exposed to the aromatization catalyst is about 15 vol % to about 70 vol % based on the total volume of the oxygenate feeds and pyrolysis oil feed.

5. The method of claim 1, wherein the total volume percentage of pyrolysis oil feed exposed to a conversion catalyst is at least about 50 vol % based on the total volume of the oxygenate feeds and pyrolysis oil feed.

6. The method of claim 1, wherein the at least one element from Groups 8-14 is selected from the group consisting of Zn, Ga, Ag and combinations thereof.

7. A method for converting oxygenates to aromatics, comprising:

introducing an oxygenate feed comprising methanol and having an effective hydrogen index of at least about 1 and a pyrolysis oil feed into a conversion reaction system at a plurality of feed entry points, the reaction system having a direction of flow, each of the plurality of feed entry points being located at a different location of the reaction system relative to the direction of flow, the plurality of feed entry points comprising at least a first upstream entry point and a final downstream entry point;

exposing the portions of the oxygenate feed and the pyrolysis oil feed introduced at each of the plurality of feed entry points to an aromatization catalyst to react methanol with pyrolysis oil to form a plurality of converted effluents comprising one or more aromatic compounds, at least a portion of the converted effluents from upstream feed entry points being combined with the portions of the oxygenate feed and the pyrolysis oil feed introduced at a downstream feed entry point;

wherein the volume percentage of the pyrolysis oil feed based on the total volume of the oxygenate feed and the pyrolysis oil is greater than the volume percentage of the portion of the pyrolysis oil feed introduced at the first upstream entry point based on the total volume of the portion of the pyrolysis oil feed and the portion of the oxygenate feed introduced at the first upstream entry point, and wherein said aromatization catalyst comprises ZSM-5 and at least one metal from Groups 8-14 of the Periodic Table.

8. The method of claim 7, wherein the volume percentage of the portion of the pyrolysis oil feed introduced at each feed entry point is greater than the volume percentage of the portion of the pyrolysis oil feed introduced at upstream feed entry points, the volume percentage of the portion of the pyrolysis oil feed being based on the total volume of the portions of the oxygenate feed and the pyrolysis oil feed introduced at the same entry point.

9. The method of claim 7, wherein the volume percentage of the portion of the pyrolysis oil feed introduced at least two feed entry points is substantially similar, the volume percentage of the portion of the pyrolysis oil feed being based on the total volume of the portions of the oxygenate feed and the pyrolysis oil feed introduced at the same entry point.

10. The method of claim 7, wherein the volume percentage of the portion of the pyrolysis oil feed introduced to at least one feed entry point is about 25 vol % to about 70 vol % based on the total volume of the portions of the oxygenate feed and the pyrolysis oil feed introduced at the same entry point.

11. The method of claim 7, wherein the total volume percentage of the pyrolysis oil feed exposed to the aromatization catalyst is about 15 vol % to about 70 vol % based on the total volume of the oxygenate feed and the pyrolysis oil feed.

12. The method of claim 7, wherein the total volume percentage of pyrolysis oil feed exposed to the aromatization catalyst is at least about 50 vol % based on the total volume of the oxygenate feed and the pyrolysis oil feed.

13. The method of claim 7, wherein the at least one element from Groups 8-14 is selected from the group consisting of Zn, Ga, Ag and combinations thereof.

* * * * *